US011759393B2

(12) United States Patent
Zakaria et al.

(10) Patent No.: US 11,759,393 B2
(45) Date of Patent: Sep. 19, 2023

(54) PRESCRIPTION MEDICINE PACKAGING SYSTEM AND METHOD FOR USING SAME TO PROVIDE RANGE OF COMPLIANCE OPTIONS

(71) Applicants: Hassan Zakaria, Midlothian, VA (US); Matthew Gaal, Gelang Patah (MY)

(72) Inventors: Hassan Zakaria, Midlothian, VA (US); Matthew Gaal, Gelang Patah (MY)

( * ) Notice: Subject to any disclaimer, the term of this patent is extended or adjusted under 35 U.S.C. 154(b) by 269 days.

(21) Appl. No.: 17/092,363

(22) Filed: Nov. 9, 2020

(65) Prior Publication Data

US 2022/0142861 A1 May 12, 2022

(51) Int. Cl.

*A61J 1/03* (2023.01)
*G16H 40/67* (2018.01)
*G16H 20/13* (2018.01)

(52) U.S. Cl.

CPC .............. *A61J 1/035* (2013.01); *G16H 20/13* (2018.01); *G16H 40/67* (2018.01); *A61J 2200/30* (2013.01)

(58) Field of Classification Search

CPC ........ A61J 1/035; A61J 2200/30; B65D 75/36
See application file for complete search history.

(56) References Cited

U.S. PATENT DOCUMENTS 3,948,394 A * 4/1976 Hellstrom ............ B65D 75/326 206/520
5,325,968 A * 7/1994 Sowden ................ B65D 50/06 206/534.2
6,691,870 B1 * 2/2004 Palm ...................... B65D 75/36 206/461
7,121,409 B1 * 10/2006 Hamilton ............ B65D 75/585 222/541.6
9,216,850 B2 * 12/2015 Bowers ................ B65D 75/327
9,375,384 B2 * 6/2016 Webster .................. A61J 1/035
9,717,650 B2 * 8/2017 Johnston ............. B65D 75/367
11,478,404 B2 * 10/2022 Hazen .................. B42D 25/328
2003/0213721 A1 * 11/2003 Jones .................. B65D 75/367 206/528
2004/0182739 A1 * 9/2004 Williams-Hartman ..................... B65D 75/36 206/531
2011/0162330 A1 * 7/2011 Cotton .............. B65D 83/0463 53/476
2013/0256183 A1 * 10/2013 Ingraham ............ B65D 75/327 53/485
2015/0021224 A1 * 1/2015 Vossoughi ......... B65D 73/0057 206/469
2015/0096920 A1 * 4/2015 Trombley .............. A61J 1/035 206/531
2019/0282503 A1 * 9/2019 McKinney ................ A61P 3/10
2020/0165045 A1 * 5/2020 Kondo .................. B65D 75/36

* cited by examiner

*Primary Examiner* — Ernesto A Grano
*Assistant Examiner* — Symren K Sanghera
(74) *Attorney, Agent, or Firm* — Peter J. Van Bergen

(57) ABSTRACT

A prescription medicine packaging system includes cells. Each cell stores prescription medicine. Each cell has an opening adapted for access by a user. A cap is aligned over and seals each opening. Each cap includes a first part and a second part that are independent of one another and uniquely identifiable by features thereof. Each of the caps is breached via one of removal and destruction of one of its first part and second part.

6 Claims, 3 Drawing Sheets

PRESCRIPTION MEDICINE PACKAGING SYSTEM AND METHOD FOR USING SAME TO PROVIDE RANGE OF COMPLIANCE OPTIONS

FIELD OF THE INVENTION

The invention relates generally to medicine packaging, and particularly to a packaging system for prescription medicine as well as a method for using the packaging system to satisfy a range of patient compliance options.

BACKGROUND OF THE INVENTION

Physicians prescribe medicines for their patients for a variety of conditions and diseases. In many cases, adherence to or compliance with a prescribed dosing regimen is critical for treatment efficacy and safety. For most patients, deviations from prescribed dosing requirements are of little concern. However, intentional or unintentional deviations from dosing requirements by patients with mental, emotional, or dependency issues can produce serious consequences.

To address these concerns, a variety of "smart" prescription medicine packaging systems have been developed. Many of these systems involve the inclusion of electronic sensors and/or transmitters that function as part of a monitoring system to track a patient's compliance with dosing requirements. However, given that prescription medicine packaging systems are discarded after use, the costs of such packaging systems is generally prohibitive, especially if they were to be instituted "across the board" for all types of patients.

SUMMARY OF THE INVENTION

Accordingly, it is an object of the present invention to provide a prescription medicine packaging system.

Another object of the present invention is to provide a prescription medicine packaging system that can satisfy the needs of patients not required to participate in a compliance program as well as those required to participate in a compliance program.

Still another object of the present invention is to provide a prescription medicine packaging system that is cost effective.

Yet another object of the present invention is to provide a prescription medicine packaging system that is readily adapted to existing prescription medicine packaging technologies.

A still further object of the present invention is to provide a non-electronic prescription medicine packaging system for use in a patient compliance program.

Other objects and advantages of the present invention will become more obvious hereinafter in the specification and drawings.

In accordance with the present invention, a prescription medicine packaging system includes a plurality of cells. Each cell stores prescription medicine. Each cell has an opening adapted for access by a user. A cap is aligned over and seals one cell opening. Each cap includes a first part and a second part. The first part and second part are independent of one another and are uniquely identifiable by features thereof. Each of the caps is breached via one of removal and destruction of one of its first part and second part.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
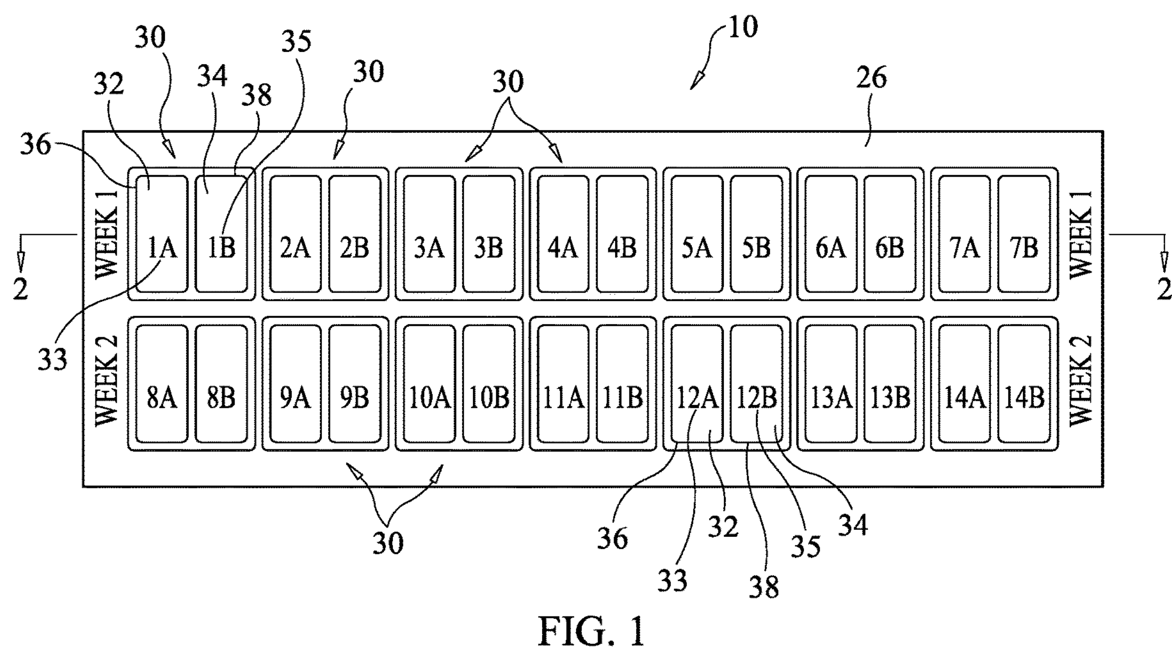
FIG. 1 is a plan view of a prescription medicine packaging system in accordance with an embodiment of the present invention.

Referring now to the drawings, simultaneous reference will be made to FIGS. 1 and 2 where a prescription medicine packaging system is shown and is referenced generally by numeral 10. In general, packaging system 10 is used for dispensing prescription medicines that are in a solid form to include tablets, capsules, caplets, etc., the choice of which is not a limitation of the present invention. Similarly, the type of prescription medicine is not a limitation of the present invention. In the illustrated example, packaging system 10 is configured for periodic (e.g., daily) dosing over the course of two weeks. However, it is to be understood that the novel features of packaging system 10 can be applied to any dosing regimen without departing from the scope of the present invention.

One of the great advantages of the present invention is its ready adaptability to existing prescription medicine packaging technologies. For example, the present invention can be used with existing blister pack technologies that are used extensively for dispensing prescription medicines. With reference now to FIG. 2, packaging system 10 includes a portion 20 that defines a plurality of cells 22, each of which has an opening indicated by dashed lined 24. Cells 22 can be coupled to or integrated with a base 26 that connects all cells 22 as is well understood in the art. For example, portion 20 can be constructed as a conventional blister pack. Disposed in each cell 22 is prescription medicine for a patient. For example, a cell 22 can contain a single dose of a medicine, multiple doses of a medicine, or multiple diverse medicines that are taken by a patient at a time of dosing. For simplicity of illustration and for purposes of the remainder of the description, each cell 22 contains a single dose of a prescription medicine 100 in a solid form thereof.

Each opening 24 is covered and sealed by a cap 30 coupled to base 26. For example, each cap 30 could be a film element adhered about its perimeter to base 26. Each cap 30 is a multi-part cap structure having two or more parts that are independent of one another. By way of an illustrative example, cap 30 includes a first part 32 and a second part 34. Parts 32 and 34 are fully integrated portions of cap 30, but are independent of one another. Specifically, parts 32 and 34 are configured for independent removal or destruction in a way that leaves the non-removed or non-destroyed part of the cap intact. For example, when caps 30 are film elements, part 32 could be made independently removable along a score line 36 circumscribing part 32, and part 34 could be made independently removable along a score line 38 circumscribing part 34. Such scoring of film elements for removal of parts thereof is well understood in the art. Parts 32 and 34 can be similarly or uniquely shaped, and/or can be rectangular (as shown) but could also be other geometric shapes (e.g., circles, triangles, etc.) without departing from the scope of the present invention.

Each of parts 32 and 34 incorporates uniquely identifiable feature(s) on its exposed surface, i.e., on the surface thereof facing away from its cell 22. In the illustrated example, the uniquely identifiable features are alphanumeric characters 33 on part 32 and alphanumeric characters 35 on part 34. For example, the alphanumeric characters could specify the number of the dose in the regimen (i.e., 1, 2, 3, etc.) and the first or second part of the cap (i.e., A or B).

Access to a cell 22 and its stored dose 100 can be achieved by removal and/or destruction of a cap's part 32 and/or the cap's part 34. For patients that are not at risk for dosing deviation problems, packaging system 10 can be used in a conventional manner without the need for any special instructions. That is, it does not matter if a patient accesses a cell 22 by removal/destruction of one or both of parts 32 and 34. However, packaging system 10 can also be used as part of a prescription medicine compliance program as will be explained later below.

Figure 2:
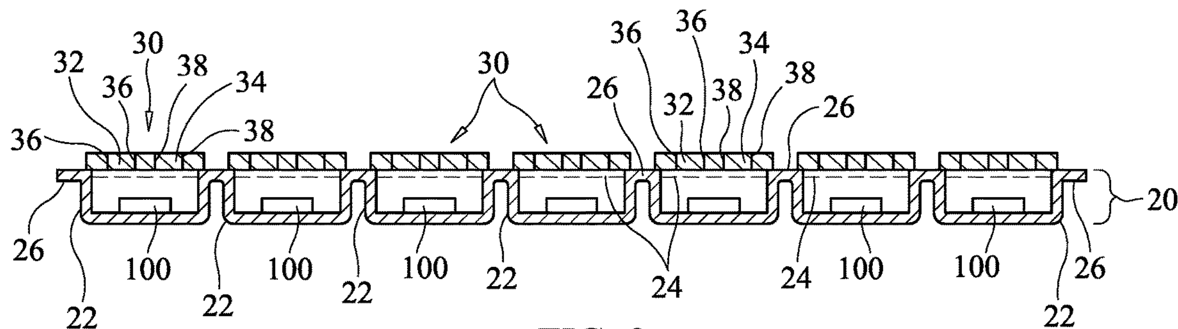
FIG. 2 is a cross-sectional view of the embodiment in FIG. 1 taken along line 2-2 thereof.
Figure 3:
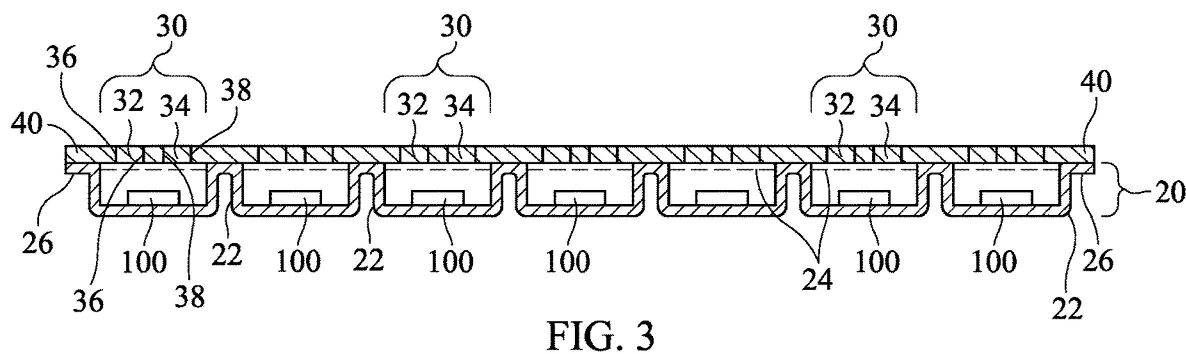
FIG. 3 is a cross-sectional view of a portion of a prescription medicine packaging system whose caps are incorporated into a sealing film in accordance with another embodiment of the present invention.

Referring now to FIG. 3, another embodiment of a prescription medicine packaging system in accordance with the present invention is shown in a cross-sectional view similar to that shown in FIG. 2. In the FIG. 3 embodiment, portion 20 has its base 26 and opening 24 completely covered by an overlay (e.g., a film) 40 having the above-described caps 30 integrated into overlay 40. Each of caps 30 has its independent and uniquely identifiable first part and second part 34 associated therewith as described above.

Figure 4:
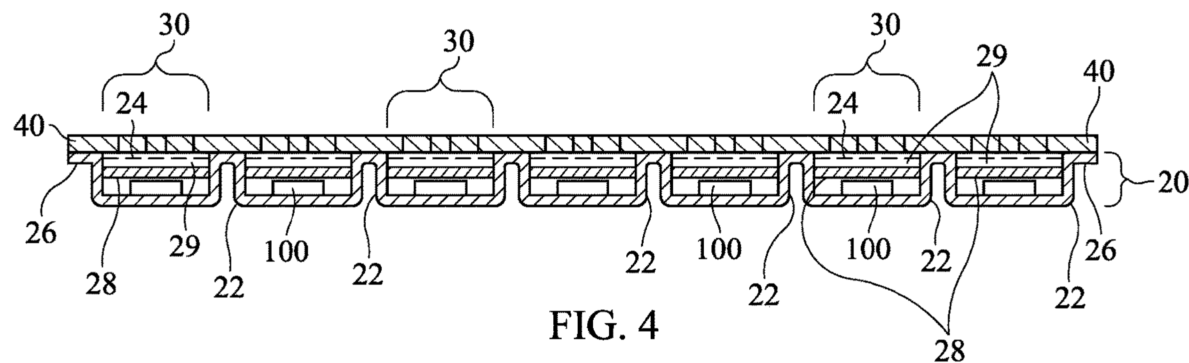
FIG. 4 is a cross-sectional view of a portion of a prescription medicine packaging system incorporating a tearable seal hidden beneath each cap in accordance with another embodiment of the present invention.

The present invention can also include additional child safety features as illustrated in the embodiment shown in FIG. 4 where a cross-sectional view similar to that shown in FIG. 2 is shown. In the FIG. 4 embodiment, overlay 40 defining caps 30 is coupled to portion 20 as described above. In addition, each cell 22 has a tearable material 28 spanning the cell and sealed to the side walls thereof. Each tearable material 28 is disposed beneath a corresponding opening 24 such that a chamber 29 is defined between a corresponding cap 30 and tearable material 28. In order to dispense dose 100, cell 22 must be pressed such that dose 100 tears or ruptures material 28 so that dose 100 is pressed into chamber 29 where it can then be accessed as described above. The extra step required to access dose 100 provides for child safety.

Figure 5A:
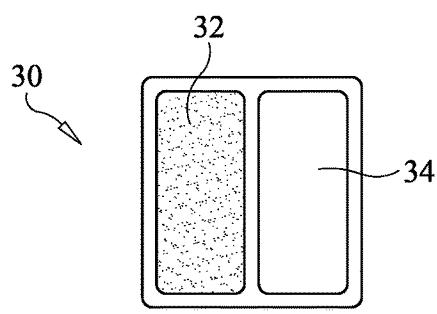
FIG. 5A is a plan view of a cap whose two parts are uniquely identifiable by color features.
Figure 5B:
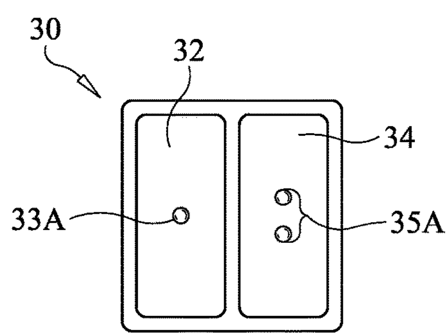
FIG. 5B is a plan view of a cap whose two parts are uniquely identifiable by relief features.
Figure 5C:
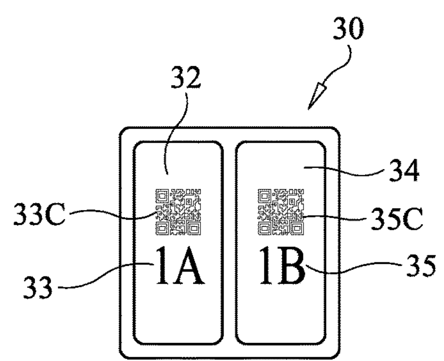
FIG. 5C is a plan view of a cap whose two parts are uniquely identifiable by machine-readable features and visual character features.

The uniquely identifiable features of parts 32 and 34 are not limited to the use of alphanumeric characters as the features could comprise one or more of visual features, tactile features, and machine-readable features. For example, FIG. 5A illustrates a cap 30 whose first part 32 is one color and second part 34 is a distinct color from that used for part 32. FIG. 5B illustrates a cap 30 whose first part 32 has a unique relief element (e.g., a Braille letter) as compared to the relief element on second part 34. In the illustrated example, part 32 presents the Braille symbol referenced by numeral 33A for the letter "a" and part 34 presents the Braille symbol referenced by numeral 35A for the letter "b". FIG. 5C illustrates the use of a combination of a machine-readable QR code 33C and alphanumeric characters 33 on part 32, and a QR code 35C and alphanumeric characters 35 on part 34.

Figure 6:
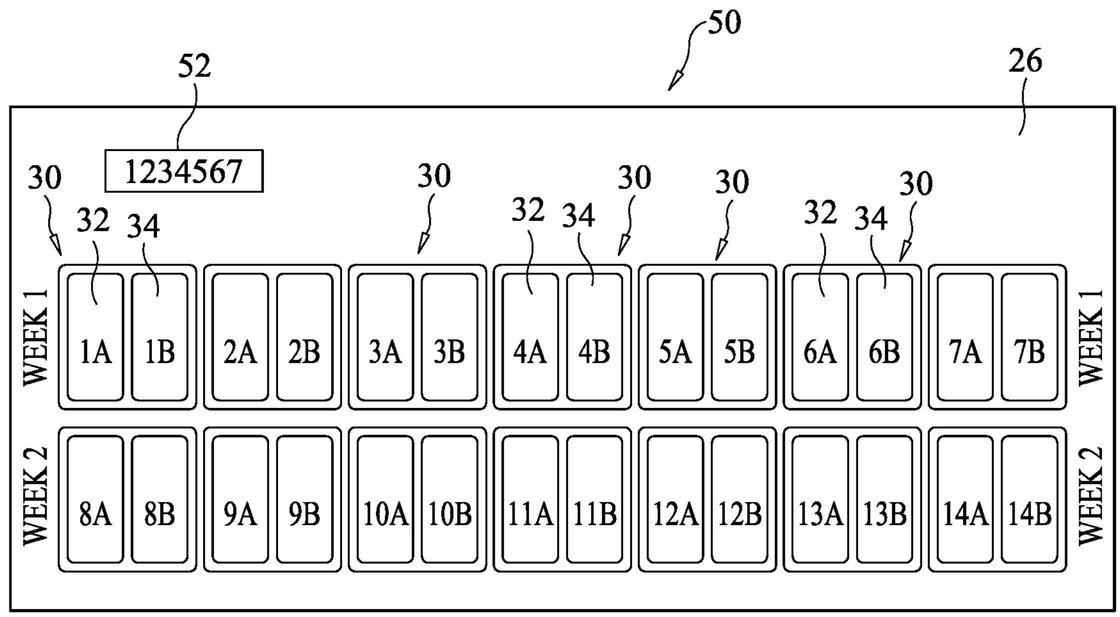
FIG. 6 is a plan view of a prescription medicine packaging system having a unique serial number assigned thereto that facilitates use of the packaging system in a prescription medicine compliance program in accordance with an embodiment of the present invention.

As mentioned above, the packaging system of the present invention can be used to dispense medicine to a patient that presents no dosing compliance concerns. However, the present invention can also be used as an integral part of a unique prescription medicine compliance program in an effort to monitor a patient's compliance with a dosing regimen. The essential features of such a compliance program will be explained with reference to FIGS. 6 and 7 where the above-described packaging system 10 (FIGS. 1 and 2) is modified and referenced generally by numeral 50 to include a unique serial number 52 assigned during manufacture or when the packaging system is provided to a patient. Packaging system 50 is activated when serial number 52 is logged into a database (not shown) when it is provided to a user/patient. A variety of ways of assigning serial number 52 and the activating of packaging system 50 can be achieved in a variety of ways without departing from the scope of the present invention.

Once a patient has been provided with packaging system 50 and it has been activated, a notification system in accordance with the present invention is implements to issue periodic notifications to the patient governing dispensing of the prescription medicine for each dose or each day as is warranted. In general, each notification specifies which part of a cap 30 (i.e., either part 32 or part 34) is to be removed or destroyed to provide access to a cell of the packaging system so that a prescription medicine dose can be dispensed. For example, on "Day 1" of "Week 1", a notification can be issued to the patient specifying that the patient should remove part 34 (i.e., identified by "1B") to gain access to the dose of medicine. As a result, part 32 with "1A" thereon remains intact and identifiable. This process is repeated throughout the prescription regimen. That is, for purpose of patient compliance, a patient must wait for each dosage's notification prior to gaining access to a cell and its contained dose. In the illustrated example, after 14 days, the remaining and identifiable ones of parts 32 and 34 essentially define a pattern. If the patient adhered to the notification sequence, the pattern of remaining and identifiable parts of caps 30 will properly correspond to the caps' parts that should be identifiable.

The issuance of the periodic notifications can be accomplished in a variety of ways without departing from the scope of the present invention. For example, if serial number 52 is associated with a patient's phone number and/or e-mail address, the periodic notifications could be sent automatically to one or both of the patient's phone and e-mail address. The notifications can also be sent using other forms of wired or wireless communication systems without departing from the scope of the present invention. In other embodiments of a compliance program in accordance with the present invention, a patient could be required to request a notification each day or at time of dosing. For example, a patient could call, text, or e-mail their serial number 52 to a central location that would then issue the next notification.

Figure 7:
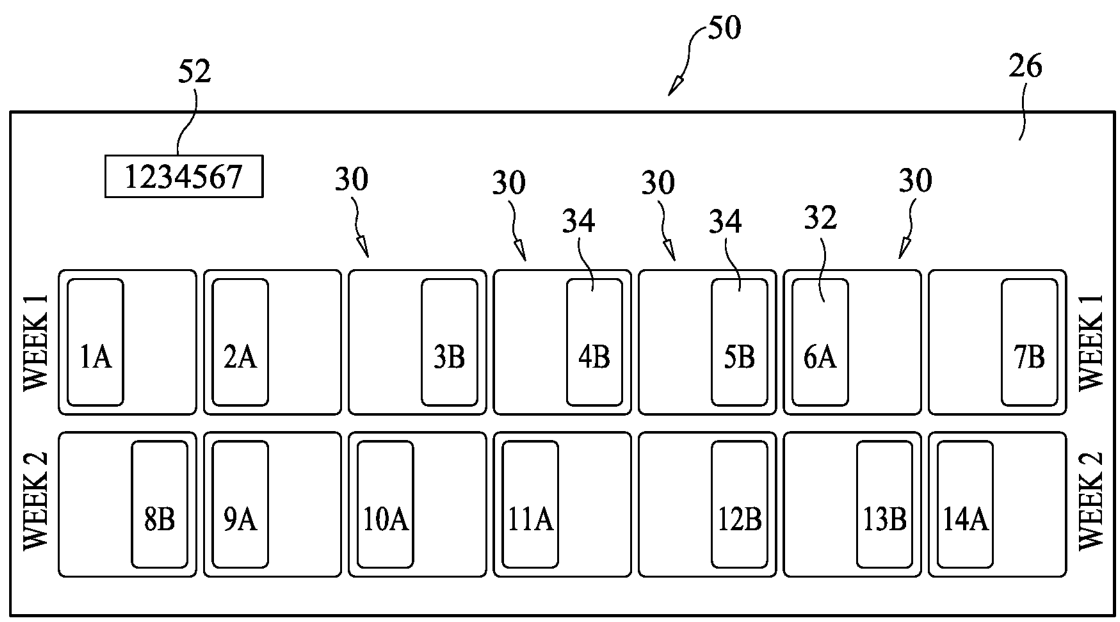
FIG. 7 is a plan view of the prescription medicine packaging system illustrated in FIG. 6 as it would appear after a patient had completed a dosing regimen in accordance with an embodiment of the prescription medicine compliance program of the present invention.

As mentioned above, at the conclusion of a prescription medicine regimen, packaging system 50 should have half of its caps' parts removed with the other half of the caps' parts remaining intact and identifiable. By way of an illustrative example, FIG. 7 illustrates packaging system 50 at the completion of a dosing regimen whose periodic notifications were as follows:

Week 1: 1B, 2B, 3A, 4A, 5A, 6B, 7A

Week 2: 8A, 9B, 10B, 11B, 12A, 13A, 14B

The remaining identifiable pattern of intact cap parts can be recorded and associated with serial number 52 as a compliance check.

Deviations from the expected pattern can be used as a treatment tool to help a patient achieve full compliance for treatment efficacy and safety. Depending on the needs of the patient and/or the nature of the medicine being dispensed, recording and/or evaluation of a package's remaining identifiable cap parts can be required daily, on a random basis, and/or when a dosing regimen is completed such that all cells of a packaging system are empty.

The advantages of the present invention are numerous. The simple packaging system can be used for any patient to include those who may need to have their dosing regimen reported and/or monitored as part of a compliance program. For cases where compliance is required, the packaging system empowers the patient with simple dosing access notification. Since the exact same packaging system can be used for patients requiring no compliance as well as those requiring compliance, there is no stigma attached to patients requiring compliance. The packaging system requires no electronics and, therefore, is a cost-effective solution to compliance monitoring. The system can be readily incorporated into existing blister pack technology thereby speeding its implementation and minimizing the need for a patient to familiarize themselves to a new type of packaging technology.

Although the invention has been described relative to a specific embodiment thereof, there are numerous variations and modifications that will be readily apparent to those skilled in the art in light of the above teachings. For example and as mentioned above, each cap in the present invention can comprise three or more independent parts without departing from the scope of the present invention. It is therefore to be understood that, within the scope of the appended claims, the invention may be practiced other than as specifically described.

What is claimed as new and desired to be secured by Letters Patent of the United States is:

1. A prescription medicine packaging system, comprising:

a blister pack having a plurality of cells, each of said cells adapted to store prescription medicine, each of said cells having an opening adapted for access by a user; and a plurality of caps coupled to said blister pack, each of said caps aligned over and sealing one said opening, each of said caps including a first removable part and a second removable part adjacent to said first removable part, said first removable part circumscribed by a first score line and said second removable part circumscribed by a second score line wherein said first removable part and said second removable part are structurally independent of one another, each of said first removable part and said second removable part being uniquely identifiable by features thereof, wherein the prescription medicine is accessible via one of removal or destruction of either of said first removable part or said second removable part.

2. A prescription medicine packaging system as in claim 1, wherein said features are selected from the group consisting of visual features, tactile features, machine readable features, and combinations thereof.

3. A prescription medicine packaging system as in claim 1, further comprising a tearable material spanning each of said cells and hidden from access by one of said caps aligned therewith.

4. A prescription medicine packaging system, comprising:

a blister pack having a plurality of cells, each of said cells adapted to store prescription medicine, each of said cells having an opening adapted for access by a user; and a plurality of caps coupled to said blister pack, each of said caps comprising a film element aligned over and sealing one said opening, each of said caps including a first part and a second part, said first part circumscribed by a first score line and said second part circumscribed by a second score line, wherein said first part and said second part are configured for one of independent removal and independent destruction, said first part and said second part being uniquely identifiable by features thereof, wherein one of said caps is breached when a selected one of said first part and said second part associated therewith is subjected to one of said independent removal and said independent destruction while a non-selected one of said first part and said second part associated therewith that is not subjected to said one of said independent removal and said independent destruction remains intact and identifiable by said features thereof.

5. A prescription medicine packaging system as in claim 4, wherein said features are selected from the group consisting of visual features, tactile features, machine readable features, and combinations thereof.

6. A prescription medicine packaging system as in claim 4, further comprising a tearable material spanning each of said cells and hidden from access by one of said caps aligned therewith.

* * * * *